(12) United States Patent
Kinami et al.

(10) Patent No.: US 10,479,809 B2
(45) Date of Patent: Nov. 19, 2019

(54) METHOD FOR PRODUCING ALKENYL PHOSPHORUS COMPOUND

(71) Applicant: MARUZEN PETROCHEMICAL CO., LTD., Chuo-ku (JP)

(72) Inventors: Yu Kinami, Ichihara (JP); Ryuichi Tenjimbayashi, Ichihara (JP); Yusuke Yokoo, Chuo-ku (JP); Ichiro Kimura, Ichihara (JP); Tomohiko Sato, Ichihara (JP); Hiroyoshi Fujino, Amagasaki (JP); Tomoko Watanabe, Amagasaki (JP); Yuta Saga, Amagasaki (JP)

(73) Assignee: MARUZEN PETROCHEMICAL CO., LTD., Chuo-ku (JP)

( * ) Notice: Subject to any disclaimer, the term of this patent is extended or adjusted under 35 U.S.C. 154(b) by 60 days.

(21) Appl. No.: 15/759,020

(22) PCT Filed: Sep. 8, 2016

(86) PCT No.: PCT/JP2016/076364
§ 371 (c)(1),
(2) Date: Mar. 9, 2018

(87) PCT Pub. No.: WO2017/043552
PCT Pub. Date: Mar. 16, 2017

(65) Prior Publication Data
US 2019/0263847 A1    Aug. 29, 2019

(30) Foreign Application Priority Data
Sep. 11, 2015   (JP) .................................. 2015-179103

(51) Int. Cl.
*C07F 9/40* (2006.01)
(52) U.S. Cl.
CPC ...................................... *C07F 9/40* (2013.01)
(58) Field of Classification Search
None
See application file for complete search history.

(56) References Cited

U.S. PATENT DOCUMENTS

2013/0126805 A1    5/2013   Hill et al.

FOREIGN PATENT DOCUMENTS

| EP | 1 369 422 A1 | 12/2003 |
|---|---|---|
| JP | 2004-26655 A | 1/2004 |

(Continued)

OTHER PUBLICATIONS

Combined Chinese Office Action and Search Report dated Apr. 4, 2019 in Patent Application No. 201680052078.5, citing documents AA and AX therein, 8 pages (with English Translation of Category of Cited Documents).

(Continued)

*Primary Examiner* — Kamal A Saeed
(74) *Attorney, Agent, or Firm* — Oblon, McClelland, Maier & Neustadt, L.L.P.

(57) ABSTRACT

Provided is a method for producing an alkenyl phosphorus compound which can produce an alkenyl phosphorus compound efficiently even with a smaller amount of a catalyst used than that used conventionally, and further which can maintain catalytic activity to produce an alkenyl phosphorus compound in high yield even at a larger reaction scale, and which can also be applied to quantity synthesis at an industrial scale using a conventional batch reactor or continuous reactor.

A method for producing an alkenyl phosphorus compound, comprising:
a step of reacting a compound represented by the following formula (1):

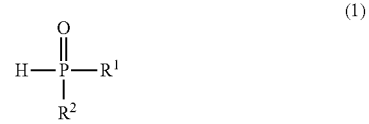

[In formula (1), $R^1$ represents $OR^3$ or $R^3$, $R^2$ represents $OR^4$ or $R^4$, and $R^3$ and $R^4$ represent, for example, each independently a substituted or unsubstituted alkyl group.]
with a compound represented by the following formula (2):

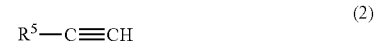

[In formula (2), $R^5$ represents, for example, a hydrogen atom, or a substituted or unsubstituted alkyl group.]
to produce the phosphorus alkenyl compound presented by at least any of the following formulas (3a) or (3b):

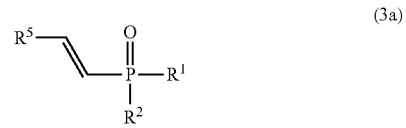

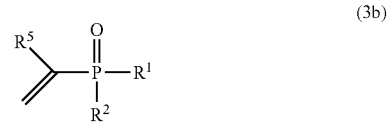

[In formulas (3a) and (3b), $R^1$ and $R^2$ have the same meaning as defined in formula (1), and $R^5$ has the same meaning as defined in formula (2).],
In which the compound represented by formula (1) is reacted with the compound represented by formula (2) using (Continued)

a transition metal catalyst, and a phosphorus oxo acid compound having an intramolecular P—H bond.

8 Claims, No Drawings

(56) References Cited

FOREIGN PATENT DOCUMENTS

| | | |
|---|---|---|
| JP | 2004-43492 A | 2/2004 |
| JP | 2004-75650 A | 3/2004 |
| JP | 2010-202718 A | 9/2010 |
| JP | 2014-87752 A | 5/2014 |
| JP | 2014-132089 A | 7/2014 |
| JP | 2015-110617 A | 6/2015 |
| WO | WO 2009/051025 A1 | 4/2009 |

OTHER PUBLICATIONS

Han, L. B. et al., "Efficient and Selective Nickel-Catalyzed Addition of H-P(O) and H-S Bonds to Alkynes", J. Am. Chem. Soc., vol. 126, No. 16, Mar. 30, 2014, pp. 5080-5081.

International Search Report dated Dec. 13, 2016 in PCT/JP2016/076364 filed Sep. 8, 2016.

Extended European Search Report dated Feb. 21, 2019 in Patent Application No. 16844413.1, citing documents AO and AX therein, 8 pages.

Goulioukina, N.S. et al. "A practical synthetic approach to chiral α-aryl substituted ethylphosphonates" Tetrahedron: Asymmetry, Pergamon, vol. 12, No. 2, XP004230914, 2001, pp. 319-327.

METHOD FOR PRODUCING ALKENYL PHOSPHORUS COMPOUND

TECHNICAL FIELD

The present invention relates to a method for producing an alkenyl phosphorus compound. More specifically, the present invention relates to a method for producing an alkenyl phosphorus compound, for example, an alkenyl phosphonic acid ester, an alkenyl phosphinic acid ester, or an alkenyl phosphine oxide compound by reacting a phosphorus compound having an intramolecular P—H bond with an acetylene compound.

BACKGROUND ART

An alkenyl phosphorus compound, for example, an alkenyl phosphonic acid ester or a alkenyl phosphinic acid ester, or an alkenyl phosphine oxide compound is a useful compound as a physiologically active substance, or as a synthetic intermediate for, for example, pharmaceuticals and/or agrochemicals. Further, an alkenyl phosphorus polymer obtained by polymerizing an alkenyl phosphorus compound is useful as a metal extractant, or as a flame retardant.

As a method for synthesizing an alkenyl phosphorus compound, there is a known method comprising reacting a phosphorus compound having an intramolecular P—H bond with an acetylene compound in the presence of a transition metal catalyst, for example a nickel catalyst, which catalyzes a hydrophosphorylation reaction. For example, Patent Literature 1 discloses that, even in a reaction producing a regioisomer, an alkenyl phosphorus compound can be obtained with high regioselectivity by carrying out the above-described reaction in coexistence with of diphenyl phosphinic acid. Further, Patent Literature 2 discloses that, by using a nickel catalyst and an acid which is a hydride donor in combination, a nickel-hydride complex is formed in a reaction system, and thus an amount of a catalyst used can be reduced to about 0.5 mol %.

As described in these Patent Literatures, a method which comprises addition of an acid to a reaction system is effective to increase catalytic activity. However, a ligand of a nickel catalyst used in the reactions of these Patent Literatures is an expensive phosphine, and thus, when one intends to produce an alkenyl phosphorus compound industrially advantageously, it is necessary to further reduce an amount of a nickel catalyst used.

In addition, the methods described in Patent Literatures 1 and 2 are studied in a very-small scale reaction system (in Examples of Patent Literatures 1 and 2, reactions are carried out with a total amount charged in a batch of on the order of several to several tens of grams). Thus, when one intends to apply the methods described in. Patent Literatures 1 and 2 to a larger reaction scale, it has been quite difficult to obtain an alkenyl phosphorus compound in high yield as a consequence of, for example, an influence of contact efficiency between a phosphorus compound as a raw material and an acetylene compound (particularly, a gaseous acetylene compound including acetylene), or catalysis deactivation by heat of reaction. In this respect, for example, Patent Literature 3 discloses that, in a method as described in Patent Literature 2, reaction yield is about 40 to 60% by a batch method, and thus it is difficult to produce an alkenyl phosphorus compound at an industrial scale (see, paragraphs [0074] to [0075]).

Additionally, in the above-described Patent Literature 3, a method for producing an alkenyl phosphorus compound using a microreactor system is proposed as a method by which an alkenyl phosphorus compound can be produced in high yield even at an industrial scale. In a microreactor, since minute quantities of a phosphorus compound and acetylene are reacted in a flow path, deactivation of a catalyst by heat of reaction can be suppressed.

However, since acetylene has low solubility in a reaction solvent, it is necessary to pass a large amount of solvent in order to pass an acetylene solution through a microreactor while gasification is suppressed (in Examples of Patent Literature 3, an amount of solvents used is more than several tens of times as much as production quantities of a vinyl phosphorus compound). Thus, the method requires an unreasonably large solvent storage equipment and separation equipment relative to production quantities, and further a large amount of a catalyst is also used to maintain catalyst concentration, and thus the method is economically extremely unfavorable.

CITATION LIST

Patent Literature

Patent Literature 1: JP 2004-043492 A
Patent Literature 2: WO 2009/051025 A
Patent Literature 3: JP 2014-087752 A

SUMMARY OF INVENTION

Technical Problem

Accordingly, an object of the present invention is to provide a method for producing an alkenyl phosphorus compound which can produce an alkenyl phosphorus compound efficiently even with a smaller amount of a catalyst than a conventional amount, and further which can maintain catalytic activity to produce an alkenyl phosphorus compound in high yield even at a larger reaction scale, and which can also be applied to quantity synthesis at an industrial scale using a conventional batch reactor or continuous reactor.

Solution to Problem

Accordingly, the present inventors, after pursuing extensive studies, surprisingly found that, in a reaction of a specific phosphorus compound having an intramolecular P—H bond and a specific acetylene compound in the presence of a transition metal catalyst, for example a nickel catalyst, which catalyzes a hydrophosphorylation reaction, when a phosphorus axe acid compound having an intramolecular P—H bond, which have never used as an acid conventionally in such a reaction because it is thought that the phosphorus acid compound reacts with an acetylene compound in the same manner as a phosphorus compound as a raw material which leads to alkenylation, is used, a desired alkenyl phosphorus compound can be obtained efficiently with a small amount of the transition metal catalyst, and catalytic activity can be maintained at both a laboratory scale and an industrial scale to provide a desired alkenyl phosphorus compound in high yield, and thus completed the present invention.

That is, the present invention provides <1> a method for producing an alkenyl phosphorus compound, comprising:
a step of reacting a compound represented by the following formula (1)

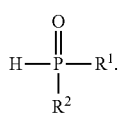

(1)

[In formula (1), $R^1$ represents $OR^3$ or $R^3$, $R^2$ represents $OR^4$ or $R^4$, and $R^3$ and $R^4$ represent each independently a substituted or unsubstituted alkyl group, a substituted or unsubstituted cycloalkyl group, a substituted or unsubstituted aralkyl group, or a substituted or unsubstituted aryl group. Further, $R^3$ and $R^4$ can be taken together to form a ring structure.] (hereinafter also referred to as phosphorus compound (1)) with a compound represented by the following formula (2):

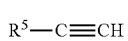

(2)

[In formula (2), $R^5$ represents a hydrogen atom, a substituted or unsubstituted alkyl group, a substituted or unsubstituted cycloalkyl group, a substituted or unsubstituted aralkyl group, a substituted or unsubstituted aryl group, a substituted or unsubstituted heteroaryl group, a substituted or unsubstituted alkenyl group, a substituted or unsubstituted alkoxy group, a substituted or unsubstituted aryloxy group, or substituted or unsubstituted silyl group.] (hereinafter also referred to as acetylene compound (2)), to produce the alkenyl phosphorus compound represented by at least any of the following formulas (3a) or (3b) (hereinafter also simply referred to as ark alkenyl phosphorus compound):

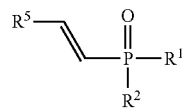

(3a)

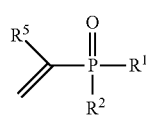

(3b)

[In formulas (3a) and (3b), $R^1$ and $R^2$ have the same meaning as defined in formula (1), and $R^5$ has the same meaning as defined in formula (2).], in which the phosphorus compound (1) reacted with the acetylene compound (2) using a transition metal catalyst, and a phosphorus oxo acid compound having an intramolecular P—H bond (hereinafter also simply referred to as a phosphorus oxo acid compound).

Further, the present invent ion provides <2> the product ion method according to the above--described <1>, in which the above-described phosphorus oxo acid compound is a compound represented by the following formula (4):

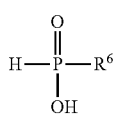

(4)

[In formula (4), $R^6$ represents a hydrogen atom, a hydroxyl group, $OR^7$, or $R^7$, and $R^7$ represents a substituted or unsubstituted alkyl group, a substituted or unsubstituted cycloalkyl group, a substituted or unsubstituted aralkyl group, or a substituted or unsubstituted aryl group]

Further, the present invention provides <3> the production method according to the above-described <1> or <2>, in which the above-described phosphorus oxo acid compound is obtained by hydrolyzing a compound represented by the following formula (5):

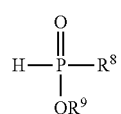

(5)

(In formula (5), $R^8$ represents a hydrogen atom, a hydroxyl up, $OR^{10}$, or $R^{10}$, and $R^9$ and $R^{10}$ represent each independently a substituted or unsubstituted alkyl group, a substituted or unsubstituted cycloalkyl group, a substituted or unsubstituted aralkyl group, a substituted or unsubstituted aryl group. Further, when $R^8$ is $OR^{10}$ or $R^{10}$, $R^9$ and $R^{10}$ can be taken together to form a ring structure) (hereinafter also referred to as phosphorus compound (5)).

Further, the present invention provides <4> the production method according to the above-described <3>, comprising applying hydrolysis treatment to the above-described phosphorus compound (5), and using the obtained hydrolysis product as the above-described phosphorus oxo acid compound.

Further, the present invention provides <5> the production method according to any of the above-described <1> to <4>, which the above-described transition metal catalyst is a nickel catalyst.

Further, the present invention provides <6> a method for producing an alkenyl phosphorus compound represented by at least any of the above-described formulas (3a) or (3b), comprising a step of applying hydrolysis treatment to phosphorus compound (1) (excluding compounds in which $R^1$ is $R^3$, and $R^2$ is $R^4$), and a step of contacting a hydrolysis product obtained by the hydrolysis treatment step with acetylene compound (2) and a transition metal catalyst.

Further, the present invent ion provides <7> the production method according to the above-described <6>, in which the above-described hydrolysis product contains the above-described phosphorus compound (1) (excluding compounds in which $R^1$ is $R^3$, and $R^2$ is $R^4$) and a compound represented by the following formula (6):

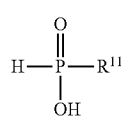

(6)

[In formula (6), $R^{11}$ represents a hydroxyl group, $OR^{12}$ represents $R^{12}$, and $R^{12}$ represents a substituted or =substituted alkyl group, a substituted or unsubstituted cycloalkyl group, a substituted or unsubstituted aralkyl group, or a substituted or unsubstituted aryl group].

Further, the present invention provides <8> the production method according to the above-described <6> or <7>, in which the above-described transition metal catalyst is a nickel catalyst.

Advantageous Effects of Invention

According to the method for producing an alkenyl phosphorus compound of the present invention, an alkenyl phosphorus compound can be produced efficiently even with a smaller amount of a catalyst than a conventional amount, and further catalytic activity can be maintained to produce an alkenyl phosphorus compound in high yield even at a larger reaction scale. Accordingly, the method for producing an alkenyl phosphorus compound of the present invention can also be applied to quantity synthesis at an industrial scale using a conventional batch reactor or continuous reactor.

DESCRIPTION OF EMBODIMENTS

<Phosphorus Compound (1)>

In the production method of the present invention, a compound represented by the following formula (1) is used as a phosphorus compound which is a raw material.

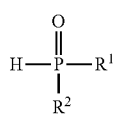

(1)

In formula (1), $R^1$ represents $OR^3$ or $R^3$, $R^2$ represents $OR^4$ or $R^4$, and $R^3$ and $R^4$ represent each independently a substituted or unsubstituted alkyl group, a substituted or unsubstituted cycloalkyl group, a substituted or unsubstituted aralkyl group, or a substituted or unsubstituted aryl group. Further, $R^3$ and $R^4$ can be taken together to form a ring structure.

An alkyl group in $R^3$ and $R^4$ is preferably an alkyl group having 1 to 12 carbon atoms, more preferably an alkyl group having 1 to 9 carbon atoms, and further more preferably an alkyl group having 1 to 6 carbon atoms.

The above-described alkyl group can be linear or branched. Examples of the alkyl group include, for example, a methyl group, an ethyl group, an n-propyl group, an isopropyl group, an n-butyl group, an isobutyl group, a sec-butyl group, a tert-butyl group, an n-pentyl group, an n-hexyl group, a 2-methylpentyl group, a 1,3-dimethylbutyl group, a 1,1,2-trimethylpropyl group, an n-heptyl group, an n-octyl group, an isooctyl group, a 2-ethylhexyl group, an n-decyl group, or an n-dodecyl group.

A cycloalkyl group in $R^3$ and $R^4$ is preferably a cycloalkyl group having 5 to 12 carbon atoms, and more preferably a cycloalkyl group having 5 to 8 carbon atoms.

Examples of the above-described cycloalkyl group include, for example, a cyclopentyl group, a cyclohexyl group, a cyclooctyl group, or a cyclododecyl group.

An aralkyl group in $R^3$ and $R^4$ is preferably an aralkyl group having 7 to 15 carbon atoms, and more preferably an aralkyl group having 7 to 10 carbon atoms.

Examples of the above-described aralkyl group include, for example, a benzyl group, a phenethyl group, a 1-naphthylmethyl group, a 2-naphthylmethyl group, a 1-naphthylethyl group, or a 2-naphthylethyl group.

An aryl group in $R^3$ and $R^4$ is preferably an aryl group having 6 to 14 carbon atoms, and more preferably an aryl group having 6 to 10 carbon atoms.

Examples of the above-described aryl group include, for example, a phenyl group, a naphthyl group, an anthryl group, a phenanthryl group, or a biphenyl group.

In $R^3$ and $R^4$, a substituent which an alkyl up may have includes, for example, an alkoxy group, a halogen atom, or a hydroxyl group. A substituent which a cycloalkyl group, an aralkyl group, or an aryl group may have includes, for example, an alkyl group, an alkoxy group, a halogen atom, a halogenated alkyl group, or a hydroxyl group.

An alkyl group in the above-described substituents preferably an alkyl group having 1 to 5 carbon atoms. Examples of the alkyl group include, for example, a methyl group, an ethyl group, an n-propyl group, an propyl group, an n-butyl group, an isobutyl group, a sec-butyl group, or a tert-butyl group. An alkoxy group in the above-described substituent is preferably alkoxy group having 1 to 5 carbon atoms. Examples of the alkoxy group include, for example, a methoxy group, an ethoxy group, a propoxy group, an isopropoxy group, an n-butoxy group, or a tert-butoxy group. A halogen atom in the above-described substituent includes a fluorine atom, a chlorine atom, a bromine atom, or an iodine atom. A halogenated alkyl group in the above-described substituent includes a group in which part or all of hydrogen atoms of the above-described alkyl group are substituted with the above-described halogen atoms.

A combination of $R^1$ and $R^2$ is preferably a combination in which $R^1$ is $OR^3$ and $R^2$ is $R^4$, or a combination in which is $OR^3$ and $R^2$ is $OR^4$, and more preferably a combination in which $R^1$ is $OR^3$ and $R^2$ is $OR^4$.

Specific examples of the phosphorus compound (1) include, for example, a phosphonic acid diester, for example, dimethyl phosphonate, diethyl phosphonate, dipropyl phosphonate, diisopropyl phosphonate, dibutyl phosphonate, diisobutyl phosphonate, di(sec-butyl) phosphonate, di(tert-butyl) phosphonate, bis(2-methylpentyl) phosphonate, bis(1,3-dimethylbutyl) phosphonate, dioctyl phosphonate, diisooctyl phosphonate, bis(2-ethylhexyl) phosphonate, didecyl phosphonate, didodecyl phosphonate, dicyclopentyl phosphonate, dicyclohexyl phosphonate, dibenzyl phosphonate, diphenyl phosphonate, ditotyl phosphonate, or dixylyl phosphonate; an organophosphinic acid ester, for example, methyl methylphosphinate, ethyl methylphosphinate, propyl methylphosphinate, isopropyl methylphosphinate, butyl methylphosphinate, isobutyl methylphosphinate, sec-butyl methylphosphinate, tert-butyl methylphosphinate, cyclohexyl methylphosphinate, phenyl methylphosphinate, methyl ethylphosphinate, ethyl ethylphosphinate, propyl ethylphosphinate, isopropyl ethylphosphinate, butyl ethylphosphinate, isobutyl ethylphosphinate, sec-butyl ethylphosphinate, tert-butyl ethylphosphinate, cyclohexyl ethylphosphinate, phenyl ethylphosphinate, methyl phenylphosphinate, ethyl phenylphosphinate, propyl phenylphosphinate, isopropyl phenylphosphinate, butyl phenylphosphinate, isobutyl phenylphosphinate, sec-butyl phenylphosphinate, tert-butyl phenylphosphinate, cyclohexyl phenylphosphinate, or phenyl phenylphosphinate; and a phosphine oxide compound, for example, dimethylphosphine oxide, diethylphosphine oxide, dipropylphosphine oxide, diisopropylphosphine oxide, dibutylphosphine oxide, diisobutylphosphine oxide, di(sec-butyl) phosphine oxide, di(tert-butyl)phosphine oxide, dicyclopentylphosphine oxide, dicyclohexylphosphine oxide, dibenzylphosphine oxide, diphenylphosphine oxide, ditolylphosphine oxide, dixylylphosphine oxide, methyl(phenyl)phosphine oxide, ethyl(phenyl)phosphine oxide, propyl(phenyl)phosphine oxide, isopropyl(phenyl)phosphine oxide, butyl(phenyl)phosphine oxide, isobutyl(phenyl)phosphine oxide, sec-butyl (phenyl)phosphine oxide, or tert-butyl (phenyl) phosphine oxide.

$R^3$ and $R^4$ can be, as described above, taken together to form a ring structure. Examples of such phosphorus compound (1) having a ring structure include, for example, 1,3,2 dioxaphospholane-2-oxide, 4,4,5,5-tetramethyl-1,3,2-dioxaphospholane-2-oxide, or 9,10-dihydro-9-oxa-10-phosphaphenanthrene-10-oxide.

Acetylene Compound (2)

Acetylene compound (2) used as a raw material in the production method of the present invention is represented by the following formula (2).

(2)

In formula (2), $R^5$ represents a hydrogen atom a substituted or unsubstituted alkyl group, a substituted or unsubstituted cycloalkyl group, a substituted or unsubstituted aralkyl group, a substituted or unsubstituted aryl group, a substituted or unsubstituted heteroaryl group, a substituted or unsubstituted alkenyl group, a substituted or unsubstituted alkoxy group, a substituted or unsubstituted aryloxy group, or a substituted or unsubstituted silyl group.

An alkyl group, a cycloalkyl group, an aralkyl group, and an aryl group in $R^5$ include each of the groups listed as $R^3$ and $R^4$ in the above-described formula (1).

A heteroaryl group in $R^5$ is an aromatic ring group containing a heteroatom (e.g., oxygen, nitrogen, or sulfur) as a constituent atom. The heteroaryl group is preferably a heteroaryl group having 4 to 12 atoms, and examples of the heteroaryl group include, for example, a thienyl group, a furyl group, a pyridyl group, or a pyrrolyl group.

An alkenyl group in $R^5$ is preferably an alkenyl group having 2 to 18 carbon atoms, and examples of the alkenyl group include, for example, a vinyl group, or a 3-butenyl group.

An alkoxy group in $R^5$ is preferably an alkoxy group having 1 to 5 carbon atoms, and examples of the alkoxy group include a methoxy group, an ethoxy group, a propoxy group, an isopropoxy group, an n-butoxy group, or a tert-butoxy group.

An aryloxy group in $R^5$ is preferably an aryloxy group having 6 to 14 carbon atoms, and examples of the aryloxy group include, for example, a phenoxy group, or a naphthyloxy group.

Examples of a silyl group in $R^5$ include, for example, a trimethylsilyl group, a triethylsilyl group, triphenylsilyl group, a phenyldimethylsilyl group, or a trimethoxysilyl group.

In $R^5$, a substituent which an alkyl group, an alkenyl group, or an alkoxy group may have includes, for example, an alkoxy group, a halogen atom, or a hydroxyl group. A substituent which a cycloalkyl group an aralkyl group, an aryl group, a heteroaryl group, an aryloxy group, and a silyl group may have includes, for example, an alkyl group, an alkoxy group, a halogen atom, a halogenated alkyl group, or a hydroxyl group. Specific examples of the substituents include each of the groups listed as substituents in $R^3$ and $R^4$ of the above-described formula (1).

Among $R^5$ as described above, a hydrogen atom, a substituted or unsubstituted alkyl group, a substituted or unsubstituted aryl group, and a substituted or unsubstituted silyl group are preferred, and a hydrogen atom is particularly preferred.

Specific examples of the acetylene compound (2) include, for example, acetylene, methylacetylene, 1-butyne, 1-hexyne, 1-octyne, 1-decene, 1-dodecene, 3-butyne-1-ol, 5-hexyne-1-ol, 1-octyne-3-chloro-1-pentyne, phenylacetylene, or trimethylsilylactylene.

Phosphorus compound (1) and acetylene compound (2) react together in a molar ratio of 1:1 stoichiometrically, but the ratio of amounts of the compounds used is not particularly limited so long as the reaction of phosphorus compound (1) and acetylene compound (2) can proceed efficiently, and the ratio is generally in a molar ratio of from 10:1 to 1:10, and preferably from 5:1 to 1:5.

The acetylene compound (2) can be used in a desired state, for example, in a gaseous form, or a liquid form. When the acetylene compound (2) is used in a liquid form, the compound can be used as a neat compound, or can be dissolved in a solvent and the resultant can be used. Solvents which can be used include those listed below as reaction solvents.

Alkenyl Phosphorus Compound

An alkenyl phosphorus compound obtained by the production method of the present invention is represented by at least any of the following formula (3a) or formula (3b).

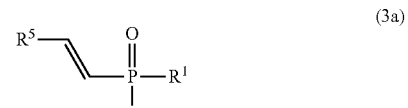
(3a)

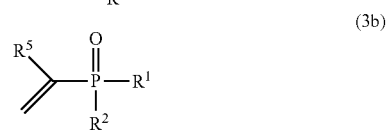
(3b)

In formulas (3a) and (3b), $R^1$ and $R^2$ have the same meaning as defined in formula (1), and $R^5$ has the same meaning as defined in formula (2).

Specific examples of the above-described alkenyl phosphorus compound include a vinylphosphonic acid diester, for example, dimethylvinylphosphonate, diethyl vinylphosphonate dipropyl vinylphosphonate, diisopropyl vinylphosphonate, dibutyl vinylphosphonate, diisobutyl vinylphosphonate, di(sec-butyl) vinylphosphonate, di(tert-butyl) vinylphosphonate, bis(2-methylpentyl) vinylphosphonate, bis(1,3-dimethylbutyl) vinylphosphonate, dioctyl vinylphosphonate, diisooctyl vinylphosphonate, bis(2-ethylhexyl) vinylphosphonate, didecyl vinylphosphonate, didodecyl vinylphosphonate, dicyclopentyl vinylphosphonate, dicyclohexyl vinylphosphonate, dibenzyl vinylphosphonate, diphenyl vinylphosphonate, ditolyl vinylphosphonate, or dixylyl vinylphosphonate; an organo(vinyl)phosphinic acid ester, for example, methyl methyl (vinyl)phosphinate, ethyl methyl(vinyl)phosphinate, propyl methyl(vinyl)phosphinate, isopropyl methyl(vinyl)phosphinate, butyl methyl (vinyl)phcsphinate, isobutylmethyl(vinyl)phosphinate, sec-butyl methyl(vinyl)phosphinate, tert-butyl methyl(vinyl) phosphinate, cyclohexyl methyl(vinyl)phosphinate, phenyl methyl(vinyl)phosphinate, methyl ethyl (vinyl)phosphinate, ethyl ethyl (vinyl)phosphinate, propyl ethyl(vinyl)phosphinate, isopropyl ethyl (vinyl)phosphinate, butyl ethyl (vinyl) phosphinate isobutyl ethyl (vinyl)phosphinate, sec-butyl ethyl (vinyl)phosphinate, tert-butyl ethyl (vinyl)phosphinate cyclohexyl ethyl (vinyl)phosphinate, phenyl ethyl (vinyl) phosphinate, methyl phenyl (vinyl)phosphinate, ethyl phenyl (vinyl)phosphinate, propyl phenyl (vinyl)phosphinate isopropyl phenyl (vinyl)phosphinate, butyl phenyl (vinyl) phosphinate, isobutyl phenyl (vinyl)phosphinate, sec-butyl phenyl (vinyl)phosphinate, tert-butyl phenyl (vinyl)phosphinate cyclohexyl phenyl (vinyl)phosphinate, or phenyl phenyl (vinyl)phosphinate and a vinylphosphine oxide compound, for example, dimethyl (vinyl) phosphine oxide, diethyl (vinyl) phosphine oxide, dipropyl (vinyl) phosphine oxide, diisopropyl (vinyl) phosphine oxide, dibutyl (vinyl) phosphine oxide, diisobutyl (vinyl) phosphine oxide di(sec-butyl) (vinyl) phosphine oxide, di(tert-butyl) (vinyl) phosphine oxide, dicyclopentyl (vinyl) phosphine oxide, dicyclohexyl (vinyl) phosphine oxide, dibenzyl (vinyl) phosphine oxide, diphenyl (vinyl) phosphine oxide, ditolyl (vinyl) phosphine oxide, dixylyl (vinyl)phosphine oxide, methyl (phenyl) (vinyl) phosphine oxide, ethyl (phenyl) (vinyl) phosphine oxide, propyl (phenyl) (vinyl) phosphine oxide, isopropyl (phenyl) (vinyl)phosphine oxide, butyl (phenyl) (vinyl)phosphine oxide, isobutyl (phenyl) (vinyl) phosphine oxide, sec-butyl (phenyl) (vinyl)phosphine oxide, or tert-butyl (phenyl) (vinyl)phosphine oxide.

An alkenyl phosphorus compound having a ring structure includes, for example, 2-vinyl 1,3,2-dioxaphospholane-2-oxide, 4,4,5,5-tetramethyl-2-vinyl-1,3,2-dioxaphospholane-2-oxide, or 9,10-dihydro-9-oxa-10-vinyl-10-phosphaphenanthrene-10-oxide.

Transition Metal Catalyst

A transition metal catalyst is not particularly limited so long as it is a transition metal catalyst which catalyzes a hydrophosphorylation reaction. A particularly preferable transition metal catalyst includes a nickel catalyst, a palladium catalyst, or a rhodium catalyst, and an industrially preferable transition metal catalyst is a nickel catalyst.

A transition metal catalyst which can be used includes those having various structures, and the transition metal catalyst is preferably a so-called low-valent transition metal catalyst, more preferably a low-valent complex to which various ligands are coordinated, and particularly preferably a low-valent complex containing a trivalent, phosphorus compound, for example a tertiary phosphine a tertiary phosphite, as a ligand.

A low-valent nickel complex containing a trivalent phosphorus compound as a ligand is not particularly limited. Specific examples of the nickel complex include, for example, dichloro bis (tricyclohexylphosphine)nickel, dichloro bis(triphenylphosphine)nickel, dimethyl bis(diphenylmethylphosphine)nickel, ethylene bis(triphenylphosphine)nickel, tetrakis(triphenylphosphine)nickel, tetrakis (diphenylmethylphosphine)nickel, tetrakis (dimethylphenylphosphine)nickel, tetrakis (trimethylphosphine)nickel, tetrakis(triethylphosphine) nickel, tetrakis(tripropylphosphine)nickel, tetrakis(tributyl-phosphine)nickel, tetrakis(trimethylphosphite)nickel, or tetrakis (triphenyl phosphite)nickel.

As a nickel complex, a cationic nickel-hydride complex as described in WO 2009/051025 A or JP 2014-087752 A can also be used. Specific examples of such a cationic nickel-hydride complex include, for example, bis(trimethylphosphine)Nickel (II) hydridophosphate.

A low-valent palladium complex containing a trivalent phosphorus compound as a ligand is not particularly limited. Specific examples of the palladium complex include, for example, dimethyl bis(triphenylphosphine)palladium, dimethyl bis(diphenylmethylphosphine)palladium, dimethyl bis (triethylphosphine)palladium, ethylene bis(triphenylphosphine)palladium, dimethyl [1,3-bis(diphenylphosphino) propane]palladium, or tetrakis(triphenylphosphine) palladium.

A low-valent rhodium catalyst containing a trivalent phosphorus compound as a ligand is not particularly limited. Specific examples of the rhodium catalyst include, for example, chloro tris(triphenylphosphine)rhodium, bromo tris(triphenylphosphine)rhodium, or chlorocarbonyl bis(trimethylphosphite)rhodium.

The transition metal catalyst can be used solely, or two or more of the transition metal catalysts can be used in combination. Further, a low-valent complex as described above can be formed in a reaction system by reacting a appropriate precursor complex, which can easily be converted into a low-valent complex with a tertiary phosphine or a tertiary phosphite.

An amount of a transition metal catalyst used is preferably 0.01 mole or more for 100 mole of phosphorus compound (1), more preferably 0.05 mole or more, and particularly preferably 0.1 mole or more, and is preferably 1 mole or less, more preferably 0.5 mole or less, and particularly preferably 0.3 mole or less. According to the production method of the present invention, by activation of a catalyst, a reaction can efficiently proceed with such a small amount of a catalyst.

Phosphorus Oxo Acid Compound Having an Intramolecular P—H Bond

A phosphorus oxo acid compound used in the production method of the present invention has a P—H bond in the molecule. Thus, it is believed that the phosphorus oxo acid compound can be alkenlylated, same manner as phosphorus compound (1), by a reaction with acetylene compound (2), and thus the phosphorus oxo acid compound has never added as an acid in a production of an alkenyl phosphorus compound conventionally. However, surprisingly, as described in the following Examples, by reacting in the presence of a phosphorus oxo acid compound having such a structure, a desired alkenyl phosphorus compound can be obtained efficiently with a small amount of a catalyst, and catalytic activity can be maintained at both a laboratory scale and an industrial scale, and thus a desired alkenyl phosphorus compound was obtained in a high yield.

In the present invention, while the causes for maintaining the catalytic activity even in a reaction system at a large reaction scale by using the above-described phosphorus oxo acid compound are not necessarily clear, it can be assumed that a phosphorus oxo acid compound used in the present invention has, unlike a conventionally used acid (e.g., phosphoric acid and diphenylphosphinic acid), a P—H bond, which reacts with a transition metal catalyst to form a bond between a transition metal atom and phosphorus atom (e.g., Ni—P bond), which results in formation of a stable and highly active catalyst having a structure, which is different from that of a conventional hydride catalyst, in a reaction system. Accordingly, the above-described phosphorus oxo acid compound is preferably brought into contact with a transition metal catalyst in advance of initiation of the reaction of phosphorus compound (1) and acetylene compound (2). Specifically, it is preferred that at least a transition metal catalyst and a phosphorus oxo acid compound, and, if required, a solvent are mixed, and the resultant is held for a certain period of time, and then a reaction is initiated. The holding time is generally about 1 to 60 minutes, and preferably about 5 to 30 minutes. The holding temperature can be at room temperature, but it is preferred to hold at the same temperature as that of the reaction conditions.

A phosphorus oxo acid compound having an intramolecular P—H bond includes a c and represented by the following formula (4).

In formula (4), $R^6$ represents a hydrogen atom, a hydroxyl group, $OR_7$, or $R^7$, and $R^7$ represents a substituted or unsubstituted alkyl group, a substituted or unsubstituted cycloalkyl group, a substituted or unsubstituted aralkyl group, or a substituted or unsubstituted aryl group.

An alkyl group, a cycloalkyl group, an aralkyl group, or an aryl group in $R^7$, and a substituent which the alkyl group, the cycloalkyl group, the aralkyl group, or the aryl group may have include each of the groups listed in $R^3$ and $R^4$ in the above-described formula (1).

$R^6$ is, from the viewpoint of stabilization of a catalyst and an activity-increasing effect ma catalyst, preferably a hydroxyl group, $OR^7$, or $R^7$, and more preferably a hydroxyl group, or $OR^7$.

Specific examples of the above-described phosphorus oxo acid compound include, for example, phosphonic acid; phosphinic acid; a phosphonic acid monoester, for example, methyl phosphonate, ethyl phosphonate, propylphosphonate, isopropyl phosphonate, butyl phosphonate, isobutyl phosphonate, sec-butyl phosphonate, tert-butylphosphonate, 2-methylpentyl phosphonate, 1,3-dimethylbutylphosphonate, octylphosphonate, isooctyl phosphonate, 2-ethylhexyl phosphonate, decyl phosphonate, dodecyl phosphonate, cyclopentyl phosphonate, cyclohexyl phosphonate, benzyl phosphonate, phenyl phosphonate, tolyl phosphonate, xylyl phosphonate, 2-hydroxyethyl, phosphonate, or (2-hydroxy-1,1,2-trimethylpropyl) phosphonate; and organophosphinic acid, for example, methylphosphinic acid, ethylphosphinic acid, propylphosphinic acid, isopropylphosphinic acid, butylphosphinic acid, isobutylphosphinic acid, sec-butylphosphinic acid, tert-butylphosphinic acid, cyclopentylphosphinic acid, cyclohexylphosphinic acid, benzylphosphinic acid, phenylphosphinic acid, tolylphosphinic acid, xylylphosphinic acid, biphenylphosphinic acid, or (2'-hydro-2-biphenyl) phosphinic acid (HBP). Among the above-described phosphorus oxo acid compound, in stabilization of a catalyst and an activity-increasing effect on a catalyst, phosphonic acid, a phosphonic acid monoester, and organophosphinic acid are preferred, and phosphonic acid and a phosphonic acid monoester are more preferred.

The above-described phosphorus oxo acid compound can be used solely, or two or more of the above-described phosphorus oxo acid compounds can be used in combination.

An amount of the above-described phosphorus oxo acid compound used is preferably in a range of from 0.01 to 10 mole for 100 mole of phosphorus compound (1), more preferably in a range of from 0.05 to 5 mole, and further more preferably in a range of from 0.1 to 3 mole.

The above-described phosphorus oxo acid compound can be used as a neat compound, or can be dissolved in a solvent and the resultant can be used. Solvents which can be used include those listed below as reaction solvents. Further the compound can be mixed with the phosphorus compound (1) and the resultant can be used.

The above-described phosphorus oxo acid compound is commercially available, but also can be synthesized by a publicly-known method. For example, the phosphorus oxo acid compound can be obtained by hydrolyzing a phosphonic acid ester or a phosphinic acid ester (hereinafter also referred to as a raw material for hydrolysis) which corresponds to the phosphorus oxo acid compound.

Hydrolysis Treatment

Then the above-described hydrolysis treatment is described below in detail.

As a rasp material for hydrolysis, a compound represented by the following formula (5) is preferred.

In formula (5), $R^8$ represents a hydrogen atom, a hydroxyl, group, $OR^{10}$, or $R^{10}$, and $R^9$ and $R^{10}$ represent each independently a substituted or unsubstituted alkyl group, a substituted or unsubstituted cycloalkyl group, a substituted or unsubstituted aralkyl group, or a substituted or unsubstituted aryl group. Further, when $R^8$ is $OR^{10}$ or $R^{10}$, $R^9$ and $R^{10}$ can be taken together to form a ring structure.

An alkyl group, a cycloalkyl group, an aralkyl group, or an aryl group in $R^9$ and $R^{10}$, and a substituent which the alkyl group, the cycloalkyl group, the aralkyl group, or the aryl group may have include each of the groups listed in $R^3$ and $R^4$ in the above-described formula (1). $R^8$ is preferably $OR^{10}$, or $R^{10}$, and particularly preferably $OR^{10}$ from the viewpoint of ease of hydrolysis.

Specific examples of the phosphorus compound (5) include a phosphonic acid diester, and an organophosphinic acid ester listed as specific examples of phosphorus compound (1); and a phosphonic acid monoester listed as a specific examples of a phosphorus oxo acid compound; and a phosphinic acid ester, for ex-ample, methyl phosphinate, ethyl phosphinate, propyl phosphinate, isopropyl phosphinate, butyl phosphinate, isobutyl phosphinate, sec-butyl phosphinate, tert-butyl phosphinate, cyclohexyl phosphinate, or phenyl phosphinate listed as specific examples of a phosphorus oxo acid compound Further, $R^9$ and $R^{10}$ can be taken together to form a ring structure as described above, and examples of such a phosphorus compound (5) having a ring structure include, for example, 1,3,2-dioxaphospholane-2-oxide, 4,4,4,5-tetramethyl-1,3,2-dioxapholane-2-oxide, or 9,10-dihydro-9-oxa-10-phosphaphenanthrene-10-oxide.

The above-described phosphorus compound (5) can be used solely, or two or more of the above-described phosphorus compounds (5) can be used in combination.

Among the above-described phosphorus compound (5), in ease of hydrolysis, a phosphonic acid diester is preferred, and a phosphonic acid dialkyl ester, for example, dimethyl phosphonate, diethyl phosphonate, dipropyl phosphonate, diisopropyl phosphonate, dibutyl phosphonate, or diisobutyl phosphonate is more preferred, and dimethyl phosphonate is specifically preferred.

Hydrolysis treatment conditions are not particularly limited, and a reaction temperature is generally in a range of from 0 to 200° C., preferably in a range of from 5 to 150° C., and more preferably in a range from 10 to 100° C. Reaction time varies depending on, for example, types of raw materials for hydrolysis, a reaction temperature, and other reaction conditions, and is generally from about several hours to about several tens hours.

An amount of water used in a hydrolysis treatment is suitably selected from a range in which a desired hydrolysis rate can be achieved, and is generally in a range of from 0.01 to 100 mole for 100 mole of a material for hydrolysis, preferably in a range of from 0.05 to 50 mole, and further more preferably in a range of from 0.1 to 30 mole.

A hydrolysis product obtained by a hydrolysis treatment generally includes, in addition to the above-described phosphorus oxo acid compound, for example, an unreacted raw material for hydrolysis, and an alcohol eliminated from an ester group. Further, when a phosphonic acid diester is used as a raw material for hydrolysis, phosphonic acid (phosphorous acid) is produced depending on hydrolysis rate. Since such an unreacted material or a byproduct does not interfere with a reaction of phosphorus compound (1) and acetylene compound (2), a hydrolysis product obtained by a hydrolysis treatment as it is can be added to a reaction system.

Since a hydrolysis product contains, in addition to a phosphorus oxo acid compound, an unreacted raw material for hydrolysis as described above, when a phosphorus compound, within phosphorus compounds (5), which can be used as a raw material to obtain an alkenyl phosphorus compound is used as a material for hydrolysis, an unreacted raw material for hydrolysis contained in a hydrolysis product as it is can be used as a phosphorus compound which is a raw material. Consequently, types of compounds, which can be impurities, can be reduced, and thus the following purification step can be simpler. When an unreacted raw material for hydrolysis is used as a phosphorus compound which is a raw material as described above, the hydrolysis rate in a hydrolysis product is preferably in a range of from 0.01 to 10 mol %, more preferably in a range of from 0.05 to 5 mol % and further more preferably in a range of from 0.1 to 3 mol %. Then, the hydrolysis rate can be calculated from a chemical composition analysis by, for example, GC, LC, or NMR, and also can be obtained by a simplified calculation using an amount of water used in a hydrolysis treatment.

A raw material for hydrolysis which can provide such a hydrolysis product is phosphorus compound (1) (excluding compounds in which $R^1$ is $R^3$, and $R^2$ is $R^4$).

That is, in the production a method of the present invention, a preferable embodiment, which can utilize an unreacted material for hydrolysis as a phosphorus compound which is a raw material, includes a method for producing an alkenyl phosphorus compound represented by at least any of formulas (3a) or (3b) comprising a step of applying hydrolysis treatment to phosphorus compound (1) (excluding compounds in which $R^1$ is $R^3$, and R is $R^4$), and a step of contacting a hydrolysis product obtained by the hydrolysis treatment step with acetylene compound (2) and a transition metal catalyst then, in the contacting step, phosphorus compound (1) in addition to the hydrolysis product, can be further added as required. Further, although an order (earlier or later) of contacting each of the ingredients with others can be any desired order, a hydrolysis product is preferably brought into contact with a transition metal catalyst, and then the resultant is brought into contact with acetylene compound (2).

In such an aspect, a hydrolysis product includes an unreacted phosphorus compound (1) (excluding compounds in which $R^1$ is $R^3$, and $R^2$ is $R^4$), and a compound represented by the following formula (6) which is a phosphorus oxo acid compound.

(6)

In formula (6), $R^{11}$ represents a hydroxyl group, $OR^{12}$, or $R^{12}$, $R^{12}$ represents a substituted or unsubstituted alkyl group, a substituted or unsubstituted cycloalkyl group, a substituted or unsubstituted aralkyl group, or a substituted or unsubstituted aryl group. An alkyl group, a cycloalkyl group, an aralkyl group, or an aryl group in $R^{12}$, and a substituent which these groups may have include each of the groups listed in $R^3$ and $R^4$ in the above-described formula (1).

Reaction Conditions and the Like

Next, reaction conditions and the like of a reaction of phosphorus compound (1) and acetylene compound (2) are described below.

In a reaction of phosphorus compound (1) and acetylene compound a solvent is not necessarily used, but the reaction can be carried out in a solvent as required.

Examples of solvent include a hydrocarbon-based solvent, for example, toluene, or xylene; an alcohol-based solvent, for example, methanol, ethanol, isopropanol, ethylene glycol, diethylene glycol, or ethylene glycol monomethyl ether; an ether-based solvent, for example, dioxane, tetrahydrofuran (THF), diisopropyl ether, or dimethoxyethane; an ester-based solvent, for example, ethyl acetate, or butyl acetate; a ketone-based solvent, for example, acetone, or methylethylketone; a nitrile-based solvent, for example, acetonitrile, or propiononitrile; and an amido-based solvent, for example, N,N-dimethylformamide (DMF)

The above-described solvent can be used solely, or two or more of the solvents can be used in combination.

When a solvent is used, an amount of a solvent used is not particularly limited. A solvent is preferably used in an amount to provide a concentration of phosphorus compound (1) in a total amount of materials charged of in a range of from 1 to 99% by mass, preferably used in an amount to provide a concentration in a range of from 10 to 97% by mass, and further more preferably used in an amount to provide a concentration in a range of from 20 to 95% by mass.

A reaction temperature is, in consideration of accelerating reaction rate and suppressing deactivation of a catalyst, preferably in a rage of from −20 to 120° C., more preferably in a range of from −15 to 70C., and further more preferably in a range of from −10 to 40° C.

A reaction pressure varies depending on, for example, types of acetylene compounds (2), a reaction temperature, and other reaction conditions, and is generally in a range of from 0.0001 to 5 MPa (absolute pressure, hereinafter the same), preferably in a range of from 0.001 to 2.5 MPa, and more preferably in a range of from 0.002 to 0.15 MPa. When acetylene compound (2) is a liquid form compound, atmospheric pressure is particularly preferred. On the other hand, when acetylene compound (2) is a gaseous form compound, a pressure in a range of from 0.002 to 0.1 MPa is particularly preferred.

Reaction time varies depending on types of phosphorus compounds (1) and acetylene compounds (2), a reaction temperature, and other reaction conditions, and is generally from about several hours to about several tens hours.

The production method of the present invention can be applied to a wide range of reaction scale of 100 mL to 2000 L in reactor volume (a total amount of materials charged of about 30 g to 1700 kg), and preferably 500 mL to 1200 L in reactor volume (a total amount of materials charged of about 200 g to 1000 kg). According to the production method of the present invention, even at a large reaction scale of 30 to 1200 L in reactor volume (a total amount of materials charged of about 15 to 1000 kg), and more preferably about 400 to 1200 L (a total amount of materials charged of about 200 to 1000 kg), a desired alkenyl phosphorus compound can be obtained efficiently.

The production method of the present invention can be carried out in a batch method, a semi-continuous method, or a continuous method.

A batch method typically includes the following steps:

a step of charging a phosphorus compound (1), a phosphorus oxo acid compound having an intramolecular P—H bond, and, if required, a solvent into a batch reactor, and then mixing the resultant, a step of heating or cooling the resultant to a predetermined reaction temperature, charging a transition metal catalyst into the above-described reactor, and bringing the transition metal catalyst into contact with the above-described phosphorus oxo acid compound for a predetermined period of time, a step of adding a predetermined amount of acetylene compound (2) to the above-described reactor to initiate a reaction, keeping a reaction temperature to proceed the reaction, and a step of removing the catalyst from the reaction mixture after completion of the reaction, and separating a desired alkenyl phosphorus compound.

A semi-continuous methodically includes the following steps:

a step of, into a reactor having a means which can feed acetylene compound (2) continuously, charging a phosphorus compound (1), a phosphorus oxo acid compound having an intramolecular P—H bond, and, if required, a solvent, and then mixing the resultant, a step of heating or cooling the resultant to a predetermined reaction temperature, charging a transition metal catalyst into the above-described reactor, and bringing the transition metal catalyst into contact with the above-described phosphorus oxo compound for a predetermined period of time, a step of continuously feeding acetylene compound (2) into the above-described reactor until the amount of the acetylene compound (2) reaches a predetermined amount to carry out a reaction, a step of further keeping reaction conditions for a predetermined period of time after the completion of feeding the acetylene compound (2) to complete the reaction, and a step of removing the catalyst from the reaction mixture after completion of the reaction, and separating a desired alkenyl phosphorus compound.

A continuous method typically includes the following steps:

a step of continuously feeding phosphorus compound (1), a transition metal catalyst, a phosphorus oxo acid compound having an intramolecular P—H bond, and, if required, a solvent into a mixing chamber whose temperature is kept at a predetermined reaction temperature to carry out premixing, a step of continuously feeding the mixture obtained from the above-described premixing into a reactor whose reaction condition is kept at predetermined reaction conditions over a predetermined period of time, a step of feeding acetylene compound (2) into the reactor through a different route than that of the above-described mixture, and bringing the acetylene compound (2) into contact with the phosphorus compound (1) in the reactor to carry out a reaction, and a step of continuously draw out the reaction mixture through an outlet of the reactor, removing the catalyst from the obtained reaction mixture, and separating a desired alkyl phosphorus compound.

Note that, since a transition metal catalyst used in the production method of the present invention is susceptible to oxygen, the above-described reactions are preferably carried out under an inert gas atmosphere, for example, nitrogen or argon atmosphere. Further, when a gaseous acetylene compound (2) is used, it is preferred that the reaction is carried out in the presence of a gas zone containing acetylene compound (2).

The removal of a catalyst from the obtained reaction mixture and separation of the desired alkenyl phosphorus compound can be carried out by a publicly-known method, for example, adsorption, chromatography, distillation, extraction, or recrystallization. Further, when a solvent is used in a reaction, the solvent can be recovered by distillation to be used again.

EXAMPLES

The present invention is described below in detail with reference to Examples, but the present invention is not limited to the following Examples.

In Examples, acid concentration is measured by neutralization titration using a solution of 0.1 mol/L of potassium hydroxide in ethanol, and whether absorption of acetylene occurs or not is confirmed by changes in the internal pressure of the reactor and flow rate of acetylene.

As a nickel catalyst, A: tetrakis(trimethylphosphine)nickel, B: bis(trimethylphosphine) Nickel (II) hydridophosphate, or C: tetrakis (tributylphosphine) nickel is used.

Reference Example 1: Hydrolysis Example of Dimethyl Phosphonate (1)

To 1000 parts by mass of dimethyl phosphonate A (manufactured by SINOCHEM (China), purity of 99.08%, acid concentration of 0.13 mmol/g), 3.2 parts by mass of ion exchanged water (2.0 mol % relative to dimethyl phosphonate) was added, and a reaction was performed at room temperature for 96 hours to hydrolyze. An acid concentration of the obtained hydrolysis product A was 0.52 mmol/g. Then, the hydrolysis product A was used as it was in the following Examples 1 and 2.

Reference Example 2: Hydrolysis Example of Dimethyl Phosphonate (2)

To 1000 parts by mass of dimethyl phosphonate (manufactured by SINOCHEM (China) purity of 99.12%, acid concentration of 0.05 mmol/g), 4.9 parts by mass of ion exchanged water (3.0 mol relative to dimethyl phosphonate) was added, and a reaction was performed at 60° C. for 6 hours to hydrolyze. An acid concentration of the obtained hydrolysis product B was 0.58 mmol/g. Then, the hydrolysis product B was used as it was in the following Examples 3 to 5, and 9 to 11.

Reference Example 3: Hydrolysis Example of Dimethyl Phosphonate (3)

The hydrolysis was performed in the same manner as Reference Example 2 except that the amount of ion exchanged water used was 8.1 parts by mass (5.0 mol % relative to dimethyl phosphonate). An acid concentration of the obtained hydrolysis product C was 0.84 mmol/g. Then, the hydrolysis product C was used as it was in the following Examples 6 and 7.

Reference Example 4: Hydrolysis Example of Dimethyl Phosphonate (4)

The hydrolysis was performed in the same manner as Reference Example 2 except that the amount of exchanged water used was 2.4 parts by mass (1.5 mol % relative to dimethyl phosphonate). An acid concentration of the obtained hydrolysis product D was 0.58 mmol/g. Then, the hydrolysis product D was used as it was in the following Example 3.

Example 1: Example for Manufacturing Dimethyl Vinylphosphonate (1)

In a 1 L volume autoclave equipped with an internal thermometer, a pressure gauge, a cooling jacket, an agitator, and a gas inlet tube, 350 g of toluene and 150 g of hydrolysis product A obtained in Reference Example 1 were placed, and the interior of the sys tem was coaled to 0° C. and degassed under reduced pressure.

Then, 0.19 mol %, relative to the unreacted dimethyl phosphonate contained in hydrolysis product A, of nickel catalyst A was added, and the resultant was agitated at a rotation rate of agitating blades of 200 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 5.5 hours to obtain a desired dimethyl vinylphosphonate at a conversion ratio of 89.5%, and selectivity of 93.9%.

Example 2: Example for Manufacturing Dimethyl Vinylphosphonate (2)

A reaction was performed in the same manner as Example 1 except that the rotation rate of agitating blades was 400 rpm. The reaction was per formed for 4 hours to obtain a desired dimethyl vinylphosphonate at a conversion ratio of 84.7%, and selectivity of 92.9%.

Example 3: Example for Manufacturing Dimethyl Vinylphosphonate (3)

In a 1 L volume autoclave equipped with an internal thermometer, a pressure gauge, a cooling jacket, an agitator, and a gas inlet tube, 75 g of hydrolysis product B obtained in Reference Example 2, 75 g of dimethyl phosphonate B (manufactured by SINOCHEM (China), purity of 99.12%, acid concentration of 0.05 mmol/g), and 350 g of toluene were placed, and the interior of the system was cooled to 0° C. and degassed under reduced pressure.

Then, 0.19 mol %, relative to dimethyl phosphonate, of nickel catalyst B was added, and the resultant was agitated at a rotation rate of agitating blades of 400 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 3 hours to obtain a desired dimethyl vinylphosphonate at a conversion ratio of 78.8%, and selectivity of 95.2%.

Example 4: Example for Manufacturing Dimethyl Vinylphosphonate (4)

In a 600 L volume reaction tank equipped with an internal thermometer, a pressure gauge, a cooling jacket, an agitator, and a gas inlet tube, 63 kg of hydrolysis product B obtained in Reference Example 2, 63 kg of dimethyl phosphonate B (manufactured by SINOCHEM (China), purity of 99.12%, acid concentration of 0.05 mmol/g), and 249 kg of toluene were introduced, and the interior of the system was regulated at 5° C. ±5° C. and degassed under reduced pressure.

Then, 0.9mol %, relative to dimethyl phosphonate, of nickel catalyst A was added, and the resultant was agitated at a rotation rate of agitating blades of 150 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 6.6 hours to obtain a desired dimethyl vinylphosphonate at a conversion ratio of 76.6%, and selectivity of 95.5% (yield: 114 kg).

Example 5: Example for Manufacturing Dimethyl Vinylphosphonate (5)

In a 1200 L volume reaction tank equipped with an internal thermometer, a pressure gauge, a cooling jacket, an agitator, and a gas inlet tube, 120 kg of hydrolysis product B obtained in Reference Example 2, 120 kg of dimethyl phosphonate B (manufactured by SINOCHEM (China), purity of 99.12%, acid concentration of 0.05 mmol/g) and 560 kg of toluene were introduced, and the interior of the system was regulated at 5° C. ±5° C. and degassed under reduced pressure.

Then, 0.19 mol %, relative to dimethyl phosphonate, of nickel catalyst A was added, and the resultant was agitated at a rotation rate of agitating blades of 150 rpm for 15 minutes.

Acetylene was fed into the reaction system at a feed pressure of 0.02 MPa, and the temperature and agitation conditions were kept to proceed a reaction until an absorption of acetylene disappeared. The reaction as performed for 8 hours to obtain a desired dimethyl vinylphosphonate at a conversion ratio of 71.4%, and selectivity of 93.0% (yield: 197 kg)

Example 6: Example for Manufacturing Dimethyl Vinylphosphonate (6)

In a 1 L volume autoclave equipped with an internal thermometer, a pressure gauge, a cooling jacket, an agitator, and a gas inlet tube, 40 g of hydrolysis product C obtained in Reference Example 3, 110 g of dimethyl phosphonate B (manufactured by SINOCHEM (China), purity of 99.12%, acid concentration of 0.05 mmol/g), and 350 g of toluene were placed, and the interior of the system was cooled to 0° C. and degassed under reduced pressure.

Then, 0.19 mol %, relative to dimethyl phosphonate, of nickel catalyst A was added, and the resultant was agitated at a rotation rate of agitating blades of 400 rpm for 15 minutes.

Acetylene Baas fed into the reaction system at a feed pressure of 0.02 MPa, and the temperature and agitation conditions were kept to proceed a reaction until an absorption of acetylene disappeared. The reaction was performed for 4 hours to obtain a desired dimethyl vinylphosphonate at a conversion ratio of 81.1%, and selectivity of 96.0%.

Example 7: Example for Manufacturing Dimethyl Vinylphosphonate (7)

In a 1 L volume autoclave equipped with an internal thermometer, a pressure gauge, a cooling jacket, an agitator, and a gas inlet tube, 90 g of hydrolysis product C obtained in Reference Example 3, 60 g of dimethyl phosphonate B (manufactured by SINOCHEM (China), purity of 99.12%, acid concentration of 0.05 mmol/g), and 350 g of toluene were placed, and the interior of the system was cooled to 0° C. and degassed under reduced pressure.

Then, 0.19 mol %, relative to dimethyl phosphonate, of nickel catalyst A was added, and the resultant was agitated at a rotation rate of agitating blades of 400 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 4 hours to obtain a desired dimethyl vinylphosphonate at a conversion ratio of 73.2%, and selectivity of 93.8%.

Example 8: Example for Manufacturing Dimethyl Vinylphosphonate (8)

A reaction was performed in the same manner as Example 2 except that 150 g of hydrolysis product D obtained in Reference Example 4 was used instead of hydrolysis product A, and nickel catalyst C was used instead of nickel catalyst A. The reaction was performed for 4 hours to obtain a desired dimethyl vinylphosphonate at a conversion ratio of 79.7%, and selectivity of 95.4%.

Example 9: Example for Manufacturing Dimethyl Vinylphosphonate (9)

In a 1 L volume autoclave equipped with an internal thermometer, a pressure gauge, a cooling jacket, an agitator, and a gas inlet tube, 42 g of a hydrolysis product B obtained in Reference Example 2, 208 g of dimethyl phosphonate A (manufactured by SINOCHEM (China), purity of 99.08%, acid concentration of 0.13 mmol/g), and 250 g of toluene were placed, and the interior of the system was cooled to 0° C. and degassed under reduced pressure.

Then, 0.10 mol %, relative to dimethyl phosphonate, of a nickel catalyst A was added, and the resultant was agitated at a rotation rate of agitating blades of 400 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 4 hours to obtain a desired dimethyl vinylphosphonate at a conversion ratio of 64.1%, and selectivity of 95.8%.

Example 10: Example for Manufacturing Dimethyl Vinylphosphonate (10)

A reaction was performed in the same manner as Example 9 except that an amount of a nickel catalyst A used was 0.19 mol % relative to dimethyl phosphonate. A reaction was performed for 6 hours to obtain a desired dimethyl vinylphosphonate at a conversion ratio of 91.1%, and selectivity of 95.4%.

Example 11 Example for Manufacturing Dimethyl Vinylphosphonate (11)

In a 1 L volume autoclave equipped with an internal thermometer, a pressure gauge, a cooling jacket, an agitator, and a gas inlet tube, 35 g of a hydrolysis product B obtained in Reference Example 2, 315 g of dimethyl phosphonate A (manufactured by SINOCHEM (China), purity of 99.08%, acid concentration of 0.13 mmol/g), and 150 g of toluene were placed, and the interior of the system was cooled to 0° C. and degassed under reduced pressure.

Then, 0.10 mol %, relative to dimethyl phosphonate, of a nickel catalyst A was added, and the resultant was agitated at a rotation rate of agitating blades of 400 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 5 hours to obtain a desired dimethyl vinylphosphonate at a conversion ratio of 65.9%, and selectivity of 94.4%.

Example 12: Example for Manufacturing Dimethyl Vinylphosphonate (12)

In a 1 L volume autoclave equipped with an internal thermometer, a pressure gauge, a cooling jacket, an agitator, and a gas inlet tube, 42 g of a hydrolysis product B obtained in Reference Example 2, and 458 g of dimethyl phosphonate A (manufactured by SINOCHEM (China) purity of 99.08%, acid concentration of 0.13 mol/g) were placed, and the interior of the system was cooled to 0° C. and degassed under reduced pressure.

Then, 0.10 mol %, relative to dimethyl phosphonate, of a nickel catalyst A was added, and the resultant was agitated at a rotation rate of agitating blades of 400 rpm for 15 minutes.

Acetylene was fed into the reaction system at a feed pressure of 0.02 MPa, and the temperature and agitation conditions kept to proceed a reaction until an absorption of acetylene disappeared. The reaction was performed for 6 hours to obtain a desired dimethyl vinylphosphonate at a conversion ratio of 61.8%, and selectivity of 98.5%.

Comparative Example 1: Example for Manufacturing Dimethyl Vinylphosphonate (13)

In a 1 L volume autoclave equipped with an internal thermometer, a pressure gauge, a cooling jacket, an agitator, and a gas inlet tube, 150 g of dimethyl phosphonate B (manufactured by SINOCHEM (China), purity of 99.12%, acid concentration of 0.05 mmol/g) and 350 g of toluene were placed, and the interior of the system was cooled to 0° C. and degassed under reduced pressure.

Then, 0.17 mol %, relative to dimethyl phosphonate, of nickel catalyst A was added, and the resultant was agitated at a rotation rate of agitating blades of 200 rpm for 15 minutes.

Acetylene was fed into the reaction system at a feed pressure of 0.04 mPa, and the temperature and agitation conditions were kept to proceed a reaction until an absorption of acetylene disappeared. The reaction performed for 5 hours to obtain a desired dimethyl vinylphosphonate at a conversion ratio of 27.5%, and selectivity of 85.8%.

Comparative Example 2: Example for Manufacturing Dimethyl Vinylphosphonate (14)

A reaction was performed in the same manner as Comparative Example 1 except that 150 g of dimethyl phosphonate A (manufactured by SINOCHEM (China) purity of 99.08% acid concentration of 0.13 mmol/g) was used instead of dimethyl phosphonate B, and 1.5 g of 85% phosphoric acid aqueous solution (manufactured by KANTO CHEMICAL CO., INC.) was also added when dimethyl phosphonate A was placed. The reaction was performed for 2 hours to obtain a desired di ethyl vinylphosphonate a conversion ratio of 33.2%, and selectivity of 81.3%.

Comparative Example 3: Example for Manufacturing Dimethyl Vinylphosphonate (15)

A reaction was performed in the same manner as Comparative Example 1 except that 1.2 g of phosphoric acid (solid) (manufactured by Sigma-Aldrich, purity of 99%) was also added when dimethyl phosphonate B was placed. The reaction was performed for 2 hours to obtain a desired dimethyl vinylphosphonate at a conversion ratio of 34.8%, and selectivity of 89.5%.

Example 13: Example for Manufacturing Dimethyl Vinylphosphonate (16)

A reaction was performed in the same manner as Comparative Example 1 except that 150 g of dimethyl phosphonate A (manufactured by SINOCHEM (China), purity of 99.08%, acid concentration of 0.13 mmol/g) was used instead of dimethyl phosphonate 3, and 1 g of phosphonic acid (manufactured by Wako Pure Chemical Industries, Ltd., purity of 97%) was also added when dimethyl phosphonate A was placed. The reaction was performed for 5 hours to obtain a desired dimethyl vinylphosphonate at a conversion ratio of 61.6%, and selectivity of 98.1%.

Example 14: Example for Manufacturing Dimethyl Vinylphosphonate (17)

A reaction was performed in the same manner as Example 13 except that feed pressure of acetylene was 0.02 MPa. The reaction was performed for 6 hours to obtain a desired dimethyl vinylphosphonate at a conversion. ratio of 71.2%, and selectivity of 97.6%.

Example 15: Example for Manufacturing Dimethyl Vinylphosphonate (18)

In a 30 L volume autoclave equipped with an internal thermometer, a pressure gauge, a cooling jacket, an agitator, and a gas inlet tube, 4,500 g of dimethyl phosphonate A (manufactured by SINOCHEM (China), purity of 99.08%, acid concentration of 0.13 mmol/g), 30 g of phosphonic acid (manufactured by Wako Pure Chemical Industries, Ltd., purity of 97%), and 10,500 g of toluene were placed, and the interior of the system was cooled to 0° C. and degassed under reduced pressure.

Then, 0.19 mol %, relative to dimethyl phosphonate, of nickel catalyst A was added, and the resultant was agitated at a rotation rate of agitating blades of 200 rpm for 15 minutes.

Acetylene was fed into the reaction system at a feed pressure of 0.02 MPa, and the temperature and agitation conditions were kept to proceed a reaction until an absorption of acetylene disappeared. The reaction was performed for 16 hours to obtain a desired dimethyl vinylphosphonate at a conversion ratio of 66.2%, and selectivity of 95.4%.

TABLE 1

|  | Example | | | | | | | |
|---|---|---|---|---|---|---|---|---|
|  | 1 | 2 | 3 | 4 | 5 | 6 | 7 | 8 |
| Hydrolysis product (type) | A | A | B | B | B | C | C | D |
| Hydrolysis product (g) | 150 | 150 | 75 | 63000 | 120000 | 40 | 90 | 150 |
| Phosphonic acid (g) | — | — | — | — | — | — | — | — |
| Phosphoric acid solution (g) | — | — | — | — | — | — | — | — |
| Phosphoric acid (solid) (g) | — | — | — | — | — | — | — | — |
| Catalyst | A | A | B | A | A | A | A | C |
| Catalyst concentration (mol %) | 0.19 | 0.19 | 0.19 | 0.19 | 0.19 | 0.19 | 0.19 | 0.19 |
| Volume (L) | 1 | 1 | 1 | 600 | 1200 | 1 | 1 | 1 |
| Conversion ratio (%) | 89.5 | 84.7 | 78.8 | 76.6 | 71.4 | 81.1 | 73.2 | 79.7 |
| Selectivity (%) | 93.9 | 92.9 | 95.2 | 95.5 | 93.0 | 96.0 | 93.8 | 95.4 |

TABLE 2

|  | Example | | | |
|---|---|---|---|---|
|  | 9 | 10 | 11 | 12 |
| Hydrolysis product (type) | B | B | B | B |
| Hydrolysis product (g) | 42 | 42 | 35 | 42 |
| Phosphonic acid (g) | — | — | — | — |
| Phosphoric acid solution (g) | — | — | — | — |
| Phosphoric acid (solid) (g) | — | — | — | — |
| Catalyst | A | A | A | A |
| Catalyst concentration (mol %) | 0.10 | 0.19 | 0.10 | 0.10 |
| Volume (L) | 1 | 1 | 1 | 1 |
| Conversion ratio (%) | 64.1 | 91.1 | 65.9 | 61.8 |
| Selectivity (%) | 95.8 | 95.4 | 94.4 | 98.5 |

TABLE 3

|  | Comparative Example | | | Example | | |
|---|---|---|---|---|---|---|
|  | 1 | 2 | 3 | 13 | 14 | 15 |
| Hydrolysis product (type) | — | — | — | — | — | — |
| Hydrolysis product (g) | — | — | — | — | — | — |
| Phosphonic | — | — | — | 1 | 1 | 30 |

TABLE 3-continued

|  | Comparative Example | | | Example | | |
| --- | --- | --- | --- | --- | --- | --- |
|  | 1 | 2 | 3 | 13 | 14 | 15 |
| acid (g) |  |  |  |  |  |  |
| Phosphoric acid solution (g) | — | 1.5 | — | — | — | — |
| Phosphoric acid (solid) (g) | — | — | 1.2 | — | — | — |
| Catalyst | A | A | A | A | A | A |
| Catalyst concentration (mol %) | 0.17 | 0.17 | 0.17 | 0.17 | 0.17 | 0.19 |
| Volume (L) | 1 | 1 | 1 | 1 | 1 | 30 |
| Conversion ratio (%) | 27.5 | 33.2 | 34.8 | 61.6 | 71.2 | 66.2 |
| Selectivity (%) | 85.8 | 81.3 | 89.5 | 98.1 | 97.6 | 95.4 |

As shown in Examples 1 to 15, by performing a reaction using a phosphorus oxo acid compound having an intramolecular P—H bond, the reaction proceeded at high conversion ratio and/or selectivity (conversion ratio: 61.6 to 91.1%, and selectivity: 92.9 to 98.5%) even when a catalyst was used in half or less of the amount of that used conventionally (about 0.1 to 0.2 mol %), and thus the desired alkenyl phosphorus compound was obtained efficiently. Accordingly, according to the production method of the present invention, an amount of an expensive catalyst used can be reduced, and thus an alkenyl phosphorus compound can be produced industrially advantageously. When a reaction was performed using phosphoric acid having no P—H bond (Comparative Examples 2, and 3), or when no acid was added (Comparative Example 1), conversion ratio and/or selectivity was low (conversion ratio: 27.5 to 34.8%, and selectivity: 81.3 to 89.5%) using a catalyst in an amount of about 0.2 mol %, and thus the present invention is obviously superior.

As shown in Examples 4, 5, and 15, according to the production method of the present invention, even at a reaction scale larger than a laboratory scale, that is, 30 L or more in reactor volume (a total weight of materials charged of 15 kg or more), an alkenyl phosphorus compound can be obtained in a yield comparable to that at a laboratory scale, and thus one can understand that the production method of the present invention is also suitable for quantity synthesis at an industrial scale.

The invention claimed is:

1. A method for producing an alkenyl phosphorus compound; comprising
reacting a compound represented by formula (1):

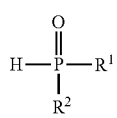

(1)

wherein $R^1$ represents $OR^3$ or $R^3$, $R^2$ represents $OR^4$ or $R^4$, and $R^3$ and $R^4$ each independently represent a substituted or unsubstituted alkyl group, a substituted or unsubstituted cycloalkyl group, a substituted or unsubstituted aralkyl group, or a substituted or unsubstituted aryl group, and $R^3$ and $R^4$ together may form a ring structure, with a compound represented by formula (2):

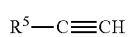

(2)

wherein $R^5$ represents a hydrogen atom, a substituted or unsubstituted alkyl group, a substituted or unsubstituted cycloalkyl group, a substituted or unsubstituted aralkyl group, a substituted or unsubstituted aryl group, a substituted or unsubstituted heteroaryl group, a substituted or unsubstituted alkenyl group, a substituted or unsubstituted alkoxy group, a substituted or unsubstituted aryloxy group, or a substituted or unsubstituted silyl group, to produce an alkenyl phosphorus compound represented by at least one formula represented by (3a) or (3b):

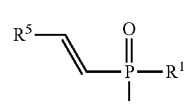

(3a)

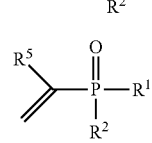

(3b)

wherein $R^1$ and $R^2$ the same meaning as defined in formula (1), and $R^5$ has the same meaning as defined in formula (2),
wherein the compound represented by the formula (1) and the compound represented by the formula (2) are reacted using a transition metal catalyst, and a phosphorus oxo acid compound having an intramolecular P—H bond.

2. The production method according to claim 1, wherein the phosphorus oxo acid compound is a compound represented by formula (4):

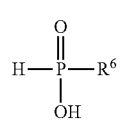

(4)

wherein $R^6$ represents a hydrogen atom, a hydroxyl group, $OR^7$, or $R^7$, and $R^7$ represents a substituted or unsubstituted alkyl group, a substituted or unsubstituted cycloalkyl group, a substituted or unsubstituted aralkyl group, or a substituted or unsubstituted aryl group.

3. The production method according to claim 1, wherein the phosphorus oxo acid compound is obtained by hydrolyzing a compound represented by Formula (5):

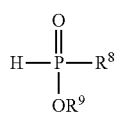

(5)

wherein $R^8$ represents a hydrogen atom, a hydroxyl group, $OR^{10}$, or $R^{10}$, and $R^9$ and $R^{10}$ each independently represent a substituted or unsubstituted alkyl group, a substituted or unsubstituted cycloalkyl group, a substituted or substituted aralkyl group, a substituted or substituted aryl group, and when $R^8$ is $OR^{10}$ or $R^{10}$, $R^9$ and $R^{10}$ together may form a ring structure.

4. The production method according to claim 3, comprising applying hydrolysis treatment to the compound represented by formula (5), and using the obtained hydrolysis product as the phosphorus oxo acid compound.

5. The production method according to claim 1, wherein the transition metal catalyst is a nickel catalyst.

6. A method for producing an alkenyl phosphorus compound, comprising:
applying hydrolysis treatment to a compound represented by formula (1), excluding compounds in which $R^1$ is $R^3$, and $R^2$ is $R^4$:

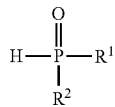
(1)

wherein $R^1$ represents $OR^3$ or $R^3$, $R^2$ represents $OR^4$ or $R^4$, and $R^3$ and $R^4$ each independently represent a substituted or unsubstituted alkyl group, a substituted or unsubstituted cycloalkyl group, a substituted or unsubstituted aralkyl group, or a substituted or unsubstituted aryl group, and $R^3$ and $R^4$ together may form a ring structure, and contacting a hydrolysis product obtained by the hydrolysis treatment with a compound represented by formula (2):

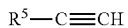
(2)

wherein $R^5$ represents a hydrogen atom, a substituted or unsubstituted alkyl group, a substituted or unsubstituted cycloalkyl group, a substituted or unsubstituted aralkyl group, a substituted or unsubstituted aryl group, a substituted, or unsubstituted heteroaryl group, substituted or unsubstituted alkenyl group, a substituted or unsubstituted alkoxy group, a substituted or unsubstituted aryloxy group, or a substituted or unsubstituted silyl group, and a transition metal catalyst, to produce an alkenyl phosphorus compound represented by at least one formula represented by (3a) or (3b):

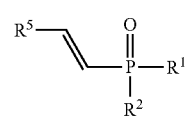
(3a)

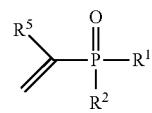
(3b)

wherein $R^1$ and $R^2$ have the same meaning as defined in formula (1), and $R^5$ has the same meaning as defined in formula (2).

7. The production method according to claim 6, wherein the hydrolysis product comprises the compound represented by formula (1),
excluding a compound in which is $R^1$ is $R^3$, and $R^2$ is $R^4$, and a compound represented by formula (6):

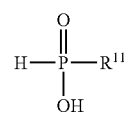
(6)

wherein $R^{11}$ represents a hydroxyl group, $OR^{12}$ represents $R^{12}$, and $R^{12}$ presents a substituted or unsubstituted alkyl group, a substituted or unsubstituted cycloalkyl group, a substituted or unsubstituted aralkyl group, or a substituted or unsubstituted aryl group.

8. The production method according to claim 6, wherein the transition metal catalyst is a nickel catalyst.

* * * * *